United States Patent
Cao et al.

(10) Patent No.: US 10,661,092 B2
(45) Date of Patent: May 26, 2020

(54) MIXTURE OF LAFESIH MAGNETIC NANOPARTICLES WITH DIFFERENT CURIE TEMPERATURES FOR IMPROVED INDUCTIVE HEATING EFFICIENCY FOR HYPERTHERMIA THERAPY

(71) Applicant: Boston Scientific Scimed, Inc., Maple Grove, MN (US)

(72) Inventors: Hong Cao, Maple Grove, MN (US); Martin R. Willard, Burnsville, MN (US); Patrick A. Haverkost, Corcoran, MN (US); Derek C. Sutermeister, Ham Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 475 days.

(21) Appl. No.: 15/286,901

(22) Filed: Oct. 6, 2016

(65) Prior Publication Data

US 2017/0100603 A1 Apr. 13, 2017

Related U.S. Application Data

(60) Provisional application No. 62/238,178, filed on Oct. 7, 2015.

(51) Int. Cl.
*A61B 18/04* (2006.01)
*A61N 2/00* (2006.01)
(Continued)

(52) U.S. Cl.
CPC ............ *A61N 2/002* (2013.01); *A61K 9/0009* (2013.01); *A61K 9/0019* (2013.01); *A61K 9/146* (2013.01);
(Continued)

(58) Field of Classification Search
CPC ...... A61K 41/052; A61N 1/403; A61N 1/406; A61N 5/025; A61B 18/04
See application file for complete search history.

(56) References Cited

U.S. PATENT DOCUMENTS

| 5,238,004 A | 8/1993 | Sahatjian et al. |
| 6,508,803 B1 | 1/2003 | Horikawa et al. |
| (Continued) | | |

FOREIGN PATENT DOCUMENTS

| CN | 108289856 | 7/2018 |
| EP | 2671570 | 12/2013 |
| (Continued) | | |

OTHER PUBLICATIONS

Ahmad, S. N. et al., "Optimszation of (Gd)5Si4 Based Materials: A Step Towards Self-controlled Hyperthermia Applications," J. Appl. Phys.,106, pp. 064701, 2009 (7 pages).
(Continued)

*Primary Examiner* — Linda C Dvorak
*Assistant Examiner* — Annabeth E Rodriguez
(74) *Attorney, Agent, or Firm* — Pauly, DeVries Smith & Deffner LLC

(57) ABSTRACT

The disclosure pertains to mixtures of LaFeSiH magnetic nanoparticles having different Curie temperatures useful for improved inductive hyperthermia efficiency, injectable formulations containing the nanoparticles, and methods of raising the temperature of selected cells using the nanoparticles.

23 Claims, 7 Drawing Sheets

(51) Int. Cl.

| | |
|---|---|
| A61K 41/00 | (2020.01) |
| A61K 9/00 | (2006.01) |
| A61K 9/51 | (2006.01) |
| A61N 1/40 | (2006.01) |
| A61K 9/14 | (2006.01) |
| B82Y 5/00 | (2011.01) |
| A61F 7/12 | (2006.01) |

(52) U.S. Cl.
CPC ............ *A61K 9/5107* (2013.01); *A61K 41/00* (2013.01); *A61K 41/0052* (2013.01); *A61N 1/406* (2013.01); *A61F 2007/126* (2013.01); *B82Y 5/00* (2013.01)

(56) References Cited

U.S. PATENT DOCUMENTS

| | | |
|---|---|---|
| 6,989,196 B2 | 1/2006 | Chatterjee et al. |
| 6,993,394 B2 | 1/2006 | Eggers et al. |
| 7,291,146 B2 | 11/2007 | Steinke et al. |
| 7,742,795 B2 | 6/2010 | Stone et al. |
| 7,842,281 B2 | 11/2010 | Haik et al. |
| 7,918,883 B2 | 4/2011 | Weber |
| 2003/0139787 A1 | 7/2003 | Eggers et al. |
| 2003/0236514 A1 | 12/2003 | Schwarz |
| 2004/0101564 A1 | 5/2004 | Rioux et al. |
| 2004/0133223 A1 | 7/2004 | Weber |
| 2004/0136905 A1 | 7/2004 | Kent et al. |
| 2004/0167506 A1 | 8/2004 | Chen |
| 2005/0021088 A1 | 1/2005 | Schuler et al. |
| 2005/0079132 A1 | 4/2005 | Wang et al. |
| 2005/0096647 A1 | 5/2005 | Steinke et al. |
| 2006/0018948 A1 | 1/2006 | Guire et al. |
| 2008/0035348 A1 | 2/2008 | Vitek et al. |
| 2008/0188912 A1 | 8/2008 | Stone et al. |
| 2008/0213382 A1 | 9/2008 | Ivkov et al. |
| 2009/0045374 A1 | 2/2009 | Lawrenz et al. |
| 2009/0081122 A1* | 3/2009 | Rufenacht .......... A61K 41/0052 424/1.29 |
| 2009/0157069 A1 | 6/2009 | Tom et al. |
| 2010/0099941 A1 | 4/2010 | Haik et al. |
| 2011/0034974 A1 | 2/2011 | Munoz et al. |
| 2011/0068290 A1 | 3/2011 | Haddon et al. |
| 2011/0166563 A1 | 7/2011 | Cheng et al. |
| 2011/0172756 A1 | 7/2011 | Doerr et al. |
| 2011/0223255 A1 | 9/2011 | Thiesen et al. |
| 2011/0275980 A1 | 11/2011 | Weber et al. |
| 2011/0295226 A1 | 12/2011 | Shohat et al. |
| 2011/0301452 A1 | 12/2011 | Maschke et al. |
| 2012/0034707 A1 | 2/2012 | Datta et al. |
| 2012/0095461 A1 | 4/2012 | Herscher et al. |
| 2012/0190911 A1 | 7/2012 | Mckenna et al. |
| 2012/0193099 A1 | 8/2012 | Vinegar et al. |
| 2012/0296326 A1 | 11/2012 | Manwaring et al. |
| 2013/0012934 A1 | 1/2013 | Manwaring et al. |
| 2013/0026978 A1 | 1/2013 | Cooley et al. |
| 2013/0165916 A1 | 6/2013 | Mathur et al. |
| 2013/0165917 A1 | 6/2013 | Mathur et al. |
| 2013/0197614 A1 | 8/2013 | Gustus et al. |
| 2013/0245357 A1 | 9/2013 | Chauhan et al. |
| 2013/0338571 A1 | 12/2013 | Chambers |
| 2014/0056982 A1 | 2/2014 | Anderson |
| 2014/0249351 A1 | 9/2014 | Jones et al. |
| 2015/0150714 A1* | 6/2015 | Anikeeva ................. A61F 7/00 607/103 |

FOREIGN PATENT DOCUMENTS

| | | |
|---|---|---|
| JP | 2011506317 | 3/2011 |
| WO | 9732532 | 9/1997 |
| WO | 02089863 | 11/2002 |
| WO | 03037202 | 5/2003 |
| WO | 03051450 | 6/2003 |
| WO | 2005084645 | 9/2005 |
| WO | 2006023261 | 3/2006 |
| WO | 2006125452 | 11/2006 |
| WO | 2012078745 | 6/2012 |
| WO | 2013096919 | 6/2013 |
| WO | 2013167147 | 11/2013 |
| WO | 2015089579 A1 | 6/2015 |
| WO | WO-2015089579 A1 * | 6/2015 ............ A61N 1/406 |

OTHER PUBLICATIONS

Akin, Y. et al., "Ni1-xCrx Alloy for Self Controlled Magnetic Hyperthermia," Crystal research and Technology, 44(4): 386-390, 2009 (5 pages).

Androlowics, et al., "Hyperthermic Ablation of Hepatic Tumors by Inductive Heating of Ferromagnetic Alloy Implants," 2003, hltp://ecommons.cornell.edu/bitstream/handle/1813/126/Ablation.pdf;sessionid=05E54F77B51462AE4A28301B41A1D549?sequence=2 (17 pages).

Atsarkin, et al., "Solution to the Bioheat Equation for Hyperthermia With La1-xAgyMnO3-d Nanoparticles: The Effect of Temperature Autostabilization," International Journal of Hypothermia, 25(3): 240-247, 2009.

Bao, et al., "Fabrication and characterization of porous poly(lactic-co-glycolic acid) (Plga) microspheres for use as a drug delivery system," J Mater Sci, vol. 46, pp. 2510-2517, 2011 (8 pages).

Berkman, et al., "The Effect of Mn Concentration on Curie Temperature and Magnetic Behavior of MOCVD Grown GaMnN Films," Researchgate.com, pp. 834, 2003, http://www.researchgate.net/publication/232027799_The_Effect_of_Mn_Concentration_on_Curie_Temperature_and_Magnetic_Behavior_of_MOCVD_Grown_GaMnN_Films (6 pages).

Bose, S. K. et al., "Exchange Interactions and Curie Temperatures in Cr-based Alloys in Zinc Blende Structure: Volume-and-Composition-Dependence," Physical Review B. 81. 10.1103/PhysRevB.81.054446 (16 pages).

Caldwell, Emily "Heat Therapy Could Be New Treatment for Parasitic Skin Disease," OSU Research Communications, 2011, https://news.osu.edu/news/2011/02/08/heattherapy/ (4 pages)/.

Chakraborti, Deepayan "Novel Diluted Magnetic Semiconductor Materials Based on Zinc Oxide," UMI, 2007, https://repository.lib.ncsu.edu/bitstream/handle/1840.16/5152/etd.pdf?sequence=1&isAllowed=y (256 pages).

"Curie Temperature," Wikipedia.com, https://en.wikipedia.org/wiki/Curie_temperature, downloaded Jul. 6, 2018 (13 pages).

"Fluidized Bed Spray Coating," Glatt GmbH (copyright 2004-2013), https://www.glatt.com/en/processes/coating/fluidized-bed-coating/ downloaded Jul. 6, 2018 (2 pages).

Giri, Jyotsnendu et al., "Investigation on Tc Tuned Nano Particles of Magnetic Oxides for Hyperthermia Applications," Biomed. Mater. Eng., 13(4): 387-399, 2003 (13 pages).

Gomez-Polo, C. et al., "Analysis of Heating Effects (Magnetic Hyperthermia) in FeCrSiBCuNb Amorphous and Nanocrystalline Wires," Journal of Applied Physics 111, 2012 (3 pages).

Habib, A. H. et al., "Evaluation of Iron-Cobalt/Ferrite Core-Shell Nanoparticles for Cancer Thermotherapy," Journal of Applied Physics, vol. 103, pp. 07A307, 2008 (3 pages).

Iorga, Alexandru et al., "Low Curie Temperature in Fe—Cr—Ni—Mn Alloys," U.P.B. Sci. Bull., Series B, vol. 73, Iss. 4, 2011 (8 pages).

Israel, Brett "Tiny Bottles and Melting Corks: Temperature Regulates New Delivery System for Drugs and Fragrances," Phys.org, 2013, https://phys.org/news/2013-09-tiny-bottles-corks-temperature-delivery.html (3 pages).

Jiang, Bo et al., "A Micro Heater Platform with Fluid Channels for Testing Micro-Solid Oxide Fuel Cell Components," Sensors and Actuators B 175 (2012) 218-224 (7 pages).

Joshi, Jay R. et al., "Role of Biodegradable Polymers in Drug Delivery," Int. J. Current Pharm. Res., 4(4): 74-81, 2012 (8 pages).

Kuznetsov, Anatoly A. et al., "Local Radiofrequency-induced Hyperthermia using CuNi Nanoparticles with Therapeudically Suitable Curie Tempertaure," J. Magn. Magn. Mater., 311: 197-203, 2007 (7 pages).

(56) References Cited

OTHER PUBLICATIONS

Litton, et al., "Zinc Oxide Materials for Electronic and Optoelectronic Device Applications," First Edition, John Wiley & Sons, 2011 (379 pages).
Liu, C. et al., "Ferromagnetism of ZnO and GaN: A Review," Journals of Material Science: Materials in Electronics, 16{9}: 555-597, 2005 (43 pages).
Martirosyan, Karen S. "Thermosensitive Magnetic Nanoparticles for Self-Controlled Hyperthermia Cancer Treatment," Nanomedicine and Nanotechnology, 3(6), 2012 (2 pages).
Mcnerny, K. L. et al., "Chemical synthesis of monodisperse γ-Fe—Ni magnetic nanoparticles with tunable Curie temperatures for self-regulated hyperthermia," Journal of Applied Physics, vol. 107, pp. 09A312{1-3}, 2010 (3 pages).
Mendelsohn, Farrell O. "Does Complete Renal Denervation Translate into Superior Clinical Outcomes? Lessons Learned From Denervation of Accessory Renal Arteries," Clinical Research in Cardiology, 103{9}:681-683, Mar. 26, 2014 (3 pages).
"Metcal, the original SmartHeat Soldering inventor," YouTube.com, published Nov. 11, 2011. https://www.youtube.com/watch?v=S9Wmqc9O24w (2 pages).
Miller, K. J. et al., "Fe—Co—Cr nanocomposites for application in self-regulated rf heating," Journal of Applied Physics, vol. 07, 2010 (3 pages).
Pana, O. et al., "Synthesis and Characterization of LSMO Nanoparticles Covered with Au Having an Core-Shell Structure," Journal of Physics: Conference Series, vol. 182, 2009 (3 pages).
"Parylene," Wikipedia.com, https://en.wikipedia.org/wiki/Parylenee, downloaded Jul. 6, 2018 (12 pages).
Pearton, S. J. et al., "Room Temperature Ferromagnetism in GaMnN and GaMnP," Phys. Stat. Sol. (a) 195, No. 1, 222-227 2003 (6 pages).
Pham, Tuan A. et al., "A Simple Approach for Immobilzation of Gold Nanoparticles on Graphene Oxide Sheets by Covalent Bonding," Applied Surface Science, vol. 257, pp. 3350-3357, 2011 (8 pages).
Prasad, A. S. et al., "Gd Substituted NiCa Ferrite/Poly Vinyl Alchohol Nanocomposite," Magn. Magn. Mater., 324: 869-872, 2012 (4 pages).
Prasad, N. K. et al., "TC-Tuned Biocompatible Suspension of La0.73SR0.27Mn03 for Magnetic Hyperthermia," J. Biomed. Mater. Res. B Appl. Biomater., 85:409-416, 2008 (8 pages).
Rehman, Jamil et al., "Ferromagnetic Self-Regulating Reheatable Thermal Rod Implants for in Situ Tissue Ablation," Journal of Endourology vol. 16(7), 2002 (9 pages).
"Response to Communication Pursuant to Rules 161(1) and 162 EPC," for European Patent Application No. 16784656.7 filed with the EPO Jul. 27, 2018 (3 pages).
Riemer, Joseph "Ultrasonic Spray Coating of Nanoparticles," Global Solar Technology, pp. 26-28, 2011 www.globalsolartechnology.com (3 pages).
Shahil, Khan M. et al., "Graphene-Based Nanocomposites as Highly Efficient Thermal Interface Materials," Graphene Based Thermal Interface Materials, 2011 (18 pages).
Shahil, Khan M. et al., "Thermal Properties of Graphene and Multilayer Graphene: Applications in Thermal Interface Materials," Solid State Communications, vol. 152, pp. 1331-1340, 2012 (10 pages).
Shimizu, et al., "Ferromagnetic Exchange Interaction and Curie Temperature of Mg1=xFe2-2xTix04 {x=0.05} System," J. Magn. Magn. Mater., 310: 1835-1837, 2007 (3 pages).
Singh, Kuldeep et al., "Polymer-Graphene Nanocomposites: Preparation, Characterization, Properties, and Applications," Nanocomposites—New Trends and Developments 37-71, 2012 (36 pages).
Skomski, R. et al., "Curie Temperature of Multiphase Nanostructures," Journal of Applied Physics 87: 9, 4756-4758, 2000 (3 pages).
"SonicSyringe Ultrasonic Dispersion Syringe Pump," Sono-Tek Corporation (2018), http://www.sono-tek.com/sonicsyringe/, downloaded Jul. 6, 2018 (2 pages).
Sperling, R. A. et al., "Surface Modification, Functionalization, and Bioconjugation of Collodial Inorganic Nanoparticles," Philosophical Transactions of the Royal Society 368:1333-1383, 2010 (51 pages).
Theodoropoulou, N. et al., "Magnetic and Structural Properties of Mn-implanted GaN," Applied Physics Letters 78:22, 3475-3477, 2001 (3 pages).
"Ultrasonic Dispersing and Deagglomeration," Hielscher Ultrasonics GmbH 2018, https://www.hielscher.com/ultrasonic-dispersing-and-deagglomeration.htm (3 pages).
Wang, B. S. et al., "Reversible Room-Temperature Magnetocaloric Effect with Large Temperature Span in Antiperovskite Compounds Ga1-xCMn3+x ,,x=0, 0.06, 0.07, and 0.08)," Journal of Applied Physics 105: 083907(1-5), 2009 (5 pages).
Wang, Xin et al., "Graphene-Based Nanocomposites," in Tech, 135-168, Apr. 19, 2011 www.intechopen.com (34 pages).
"What is Smartheat?," OkInternational, 2017 http://www.okinternational.com/metcal/english/globalnavigation/applications/hand-soldering/what-is-smartheat (2 pages).
International Search Report and Written Opinion dated (Oct. 6, 2016), for PCT/US2016/055668 (10 pages).

\* cited by examiner

MIXTURE OF LAFESIH MAGNETIC NANOPARTICLES WITH DIFFERENT CURIE TEMPERATURES FOR IMPROVED INDUCTIVE HEATING EFFICIENCY FOR HYPERTHERMIA THERAPY

PRIORITY

This application claims the benefit of priority under 35 U.S.C. § 119 to U.S. Provisional Patent Application Ser. No. 62/238,178, filed Oct. 7, 2015, which is incorporated by reference in its entirety and for all purposes.

FIELD OF THE INVENTION

The present invention concerns an injectable formulation for treatment of selected cells by alternating magnetic field induced hyperthermia, said injectable formulation comprising a liquid carrier and two or more populations of heat-generating nanoparticles. Said injectable formulation may be introduced into the vascular circulation, may be introduced directly into tissue to be heated, or may be contained within a microcatheter for insertion in proximity with tissue to be heated.

BACKGROUND OF THE INVENTION

Proliferative diseases, such as for example, cancer, represent a tremendous burden to the health-care system. Cancer, which is typically characterized by the uncontrolled division of a population of cells frequently results in the formation of a solid or semi-solid tumor, as well as subsequent metastases to one or more sites. In addition to surgery, conventional methods of cancer treatment include radiotherapy, which operates to effectuate physical damage to malignant cells so as to render them incapable of cell division, and/or chemotherapy, which generally involves systemically administering cytotoxic chemotherapeutic drugs that alter the normal structure, function or replication of DNA.

However, a problem with these approaches is that radiation in the case of radiotherapy, and chemotherapeutic drugs in the case of chemotherapy, are also toxic to normal tissues, and often create life-threatening side effects.

A very promising therapeutic approach which may be applied either alone or in combination with radiotherapy and/or chemotherapy in the treatment of cancer is hyperthermia, as indicated by recent clinical trials (M. H. Falk, R. D. Issel, "Hyperthermia in oncology", Int. J. Hyperthermia 17: 1-18 (2001); P. Wust, B. Hildebrandt, G. Sreenivasa, B. Rau, J. Gellermann, H. Riess, R. Felix.

P. Schlag, "Hyperthermia in combined treatment of cancer", The Lancet Oncology, 3: 487-497 (2002); A. Jordan, T. Rheinlander, et al. "Increase of the specific absorption rate (SAR) by magnetic fractionation of magnetic fluids", Journal of Nanoparticle Research 5 (5-6): 597-600 (2003); A. Jordan, W. Schmidt et al., "A new model of thermal inactivation and its application to clonogenic survival data for human colonic adenocarcinoma cells", Radiation Research 154(5): 600-607 (2000); A. Jordan, R Schlolz, et al., "Presentation of a new magnetic field therapy system for the treatment of human solid tumors with magnetic fluid hyperthermia", Journal of Magnetism and Magnetic Materials 225(1-2): 118-126 (2001).

Hyperthermia may be defined as a therapeutic procedure used to increase temperature of organs or tissues affected by cancer between 41 to 46° C. in order to induce apoptosis of cancer cells.

Hyperthermia, when used in combination with radiotherapy, is known to enhance radiation injury of tumor cells, and when used in combination with chemotherapy, is known to enhance chemotherapeutic efficacy.

Further, even mildly elevated temperatures are known to significantly potentiate the effects of radiotherapy and chemotherapy.

Such combinations of treatment modalities could result in lower doses of chemotherapeutic agents or radioactivity necessary to achieve a given effect, thus resulting in less toxicity.

Therefore, using hyperthermia should be considered as an advantageous treatment modality allowing to reduce life-threatening side effects caused by radiotherapy and chemotherapy.

Amongst the various techniques proposed for achieving the required temperature increase, it may be cited for example those reported in details by P. Wust, B. Hildebrandt, G. Sreenivasa, B. Rau, J. Gellermann, H. Riess, R. Felix, P. Schlag, "Hyperthermia in combined treatment of cancer" in The Lancet Oncology, 3: 487-497 (2002) and by P. Moroz, S. K. Jones and Bruce N. Gray, "Status of Hyperthermia in the Treatment of Advanced Liver Cancer", in J. Surg. Oncol. 77: 259-269 (2001).

However, these various techniques used so far to induce hyperthermia still suffer from significant limitations, the most important of which being a poor control of the heat delivered to the tumor, a poor control of the intratumoral space filling, and a poor control of the precise localization of the hyperthermic effect.

Therefore, providing a hyperthermia technique to reach a controlled temperature at moderate temperatures in a defined tumor target site is a technical challenge still under development.

Some methods for inducing a localized and targeted hyperthermia by using heat-generating nanoparticles have been proposed.

WO 01-58458 proposes a method for inducing a localized and targeted hyperthermia in a cell or tissue by delivering nanoparticles of the nanoshell type having a discrete dielectric or semiconducting core section of silica doped with rare earth emitter, or gold sulfide, surrounded by a metal conducting shell layer of gold, to said cell or tissue and exposing said nanoparticles to electromagnetic radiation under conditions wherein said nanoparticles emit heat upon exposure to said electromagnetic radiation. The core and the shell constituting the nanoparticle may be linked by using biodegradable materials such as a polyhydroxy acid polymer which degrades hydrolytically in the body, in order to facilitate the removal of the particles after a period of time.

WO 03-055469 discloses a method for inducing a localized and targeted hyperthermia by incorporating into tumor cells, through ionic targeting, nanoparticles of the shell type, having a superparamagnetic core containing iron oxide and at least two shells surrounding said core, more particularly a cationic inner shell and an anionic outer shell, and exposing said nanoparticles to electromagnetic radiation under conditions wherein said nanoparticles emit heat upon exposure to said electromagnetic radiation.

U.S. Pat. No. 6,514,481 proposes the so-called "nanoclinics" that consist in iron oxide nanoparticles in a silica shell and surrounded by a targeting agent, and optionally containing a tracking dye. Application of a constant magnetic field is thought to destroy targeted cells through a magnetically induced lysis—in contrast to the heat generation obtained under an alternative magnetic field.

U.S. Pat. No. 6,541,039 by A. Jordan and coworkers also proposes iron oxide particles, embedded in at least two shells. The outer shell having neutral and/or anionic groups allows an appropriate distribution into the tumoral tissue. The inner shell displays cationic groups to promote adsorption/absorption by the cells. The nanoparticles are injected as a suspension ("magnetic fluid") and subsequently exposed to an alternative magnetic field for hyperthermic treatment.

However, these methods do not allow the tissue to reach a controlled temperature at moderate temperatures in a defined target volume and to repeat the heating procedure in the defined target volume without repeated administration of the formulation containing nanoparticles.

JP 10-328314 discloses a shaped material implant which is invasively implanted in a bone for hyperthermia treatment, said shaped material implant comprising an alumina powder, magnetite powder having a diameter over 50 nm which is capable of generating heat in an alternating magnetic field, and a polymerized methacrylate monomer.

U.S. Pat. No. 7,918,883 discloses a magnetically heated article which employs an externally applied high frequency magnetic field in conjunction with two grades of magnetically susceptible nanomaterials having different Curie temperatures (TC1, TC2) to limit the upper temperatures to which the article will be heated upon application of an alternating magnetic field. The Curie temperature (Tc), or Curie point, is the temperature at which a ferromagnetic or a ferrimagnetic material becomes paramagnetic on heating; the effect is reversible. Upon subjecting the nanoparticles to an alternating magnetic field, self-limiting induction heating occurs as a result of magnetic hysteresis losses which ceases when the temperature of the nanoparticles reach their respective Curie temperatures.

In a disclosed application, a self-expanding Nitinol stent is heated to effect either one-way or two-way shape memory changes in the stent configuration. In an alternate application, heating to the first Curie temperature is employed to effect a one-way shape memory expansion and when the stent has deployed, further heating to the second Curie temperature is used to deliver a therapeutic agent through thermal release from a carrier. In a further alternate application, a material having an appropriate Curie temperature may be used to achieve local temperatures sufficient to inhibit restenosis by heating the cells proximate the stent to induce cell apoptosis; however the stent does not continue to heat beyond the Curie temperature which might otherwise damage the wall of vessel. In this application, the stent may be periodically reheated in situ to inhibit recurring restenosis without invasive treatment.

Barati et al. ("Extraordinary induction heating effect near the first order Curie transition", Appl. Physics Letters 105, 162412 (2014)) discloses a material having the composition $LaFe_{11.57}Si_{1.43}H_{1.75}$ and a TC of 319 K (45.85° C.), which is in the range (315 to 319 K) appropriate for hyperthermia treatment of cancerous cells. Barati further discloses that the Curie temperature may be tuned between 204 K and 350 K by altering the degree of hydrogen incorporation. In addition, Barati discloses that the family of compositions undergoes a dramatic increase in hysteresis loss near TC which has been attributed to phase coexistence in which the ferromagnetic phase is induced by a magnetic field in a matrix of the paramagnetic phase resulting in an enhanced loss power from $10\pm0.6$ $kJm^{-3}$ at 315 K to $80\pm5.7$ $kJm^{-3}$ at 317.7 K. Their analysis showed that the energy loss of the $LaFe_{11.57}Si_{1.43}H_{1.75}$ compound is highly dependent on the temperature and the expected power loss is maximized just below TC followed by immediate attenuation of the heating effect at TC. A similar increase in the induction heating effect immediately below TC is expected for rotational relaxation processes in magnetic fluids.

The Specific Absorption Rate (SAR) is a useful comparative measure of the rate at which power is absorbed per mass in these processes and usually has units of watts per kilogram (W/kg) when applied to absorption of a radio frequency (RF) electromagnetic field by the human body. SAR varies as a function of frequency (kHz) and the magnetic field intensity (H). The SAR for $LaFe_{11.57}Si_{1.43}H_{1.75}$ has been reported as 522 W/g at 279 kHz and 8.8 kA/m, while more conventional materials such FeO have been reported to exhibit a SAR of 15 (ferromagnetic) to 89 (superparamagnetic) W/g under those conditions. Similarly high SAR values are expected for $LaFe_{11.57}Si_{1.43}H_x$ over the range $0<x\leq2.27$.

While the high SAR and appropriate TC of the $LaFe_{11.57}Si_{1.43}H_x$ materials make them attractive as agents for magnetic field induced hyperthermia treatment of selected cells, the narrow temperature range (~3° C.) associated with the observed SAR enhancement and the need to raise core tissue temperatures by about 4 to 8° C. requires a combination of longer exposure times, higher fields, and/or higher frequencies than would otherwise be desirable.

SUMMARY

In some aspects, the invention relates to an injectable formulation for alternating magnetic field induced hyperthermia treatment of selected cells comprising a liquid carrier and two or more populations of nanoparticles, wherein each population of nanoparticles has a mean Curie temperature in the range 37 to 47° C. and wherein the mean Curie temperature of each population of the two or more populations of nanoparticles differs from the mean Curie temperature of each of the remaining populations of nanoparticles by at least 2° C.

In addition or alternatively, the invention relates to an injectable formulation wherein the two or more populations of nanoparticles have compositions corresponding to $LaFe_{11.57}Si_{1.43}H_x$ where $0<x\leq2.27$.

The injectable formulations include a first population of nanoparticles which has a mean Curie temperature in the range 37 to 40° C. and a second population of nanoparticles has a mean Curie temperature between a temperature 2° C. greater than mean Curie temperature of the first population of nanoparticles and 3° C. greater than mean Curie temperature of the first population of nanoparticles.

In some aspects, the injectable formulation may further comprise a third population of nanoparticles which has a mean Curie temperature between a temperature 2° C. greater than mean Curie temperature of the second population of nanoparticles and 3° C. greater than mean Curie temperature of the second population of nanoparticles.

In addition, the injectable formulation may further comprising a fourth population of nanoparticles which has a mean Curie temperature between a temperature 2° C. greater than mean Curie temperature of the third population of nanoparticles and 3° C. greater than mean Curie temperature of the third population of nanoparticles; a fifth population of nanoparticles which has a mean Curie temperature between a temperature 2° C. greater than mean Curie temperature of the fourth population of nanoparticles and 3° C. greater than mean Curie temperature of the fourth population of nanoparticles; and in some aspects may further comprise a sixth population of nanoparticles which has a mean Curie temperature between a temperature 2° C. greater than mean Curie temperature of the fifth population of nanoparticles and 3° C. greater than mean Curie temperature of the fifth population of nanoparticles.

In addition, the liquid carrier of injectable formulation may be selected from the group consisting of water, saline, dimethyl sulfoxide, ethanol, aqueous solutions of acetic acid, pyrrolidones, glycerol, and propylene glycol.

In another aspect, the liquid carrier of the injectable formulation may further comprise an in situ polymerizing component. In addition or alternatively, the liquid carrier of the injectable formulation may further comprise an in situ cross-linking component and/or a precipitating polymer component.

In some aspects, at least one of the two or more populations of nanoparticles may include an attached therapeutic agent which may include an anti-tumor agent.

In some aspects, an injectable formulation for magnetic field induced hyperthermia treatment of selected cells may comprise a liquid carrier and two or more populations of nanoparticles, wherein each population of nanoparticles has a mean Curie temperature in the range 37 to 47° C. and wherein the mean Curie temperature of each population of the two or more populations of nanoparticles differs from the mean Curie temperature of each of the remaining populations of nanoparticles by at least 2° C. such that each of the populations of nanoparticles exhibits a region of enhanced specific absorption rate within 3° C. of the respective mean Curie temperatures of the population of nanoparticles.

In such aspects, the regions of enhanced specific absorption rate of each population of nanoparticles may overlap at least one region of enhanced specific absorption rate of another population of nanoparticles and the aggregate regions of enhanced specific absorption rate may continuously span a temperature range of 5 to 10° C.

In addition or in the alternative, the aggregate regions of enhanced specific absorption rate may continuously span a temperature range of 37 to 47° C. In the alternative, the aggregate regions of enhanced specific absorption rate may continuously span a temperature range of 37 to 41° C.

In some aspects, the injectable formulation may comprise two or more populations of nanoparticles have compositions corresponding to $LaFe_{11.57}Si_{1.43}H_x$ where $0<x\leq2.27$.

In certain aspects, the liquid carrier of the injectable formulation may selected from the group consisting of water, saline, dimethyl sulfoxide, ethanol, aqueous solutions of acetic acid, pyrrolidones, glycerol, and propylene glycol. In addition or alternatively, the liquid carrier may further comprise an in situ polymerizing component, an in situ cross-linking component, and/or a precipitating polymer component.

In certain aspects, the at least one of the two or more populations of nanoparticles may include an attached therapeutic agent which may be an anti-tumor agent.

In another aspect, the invention relates to a method of heating selected cells to magnetically induce hyperthermia comprising positioning two or more populations of nanoparticles in proximity to the selected cells to be heated, wherein each population of nanoparticles has a mean Curie temperature in the range 37 to 47° C. and wherein the mean Curie temperature of each population of the two or more populations of nanoparticles differs from the mean Curie temperature of each of the remaining populations of nanoparticles by at least 2° C. and subjecting the two or more populations of nanoparticles to an alternating magnetic field, thereby causing the two or more populations of nanoparticles to generate heat locally whereupon the selected cells experience hyperthermia. In some aspects, the alternating magnetic field results in a specific absorption rate within the selected cells of no more than 2 W/kg.

In certain additional aspects local heating of at least one of the two or more populations of nanoparticles releases a therapeutic agent which may be an anti-tumor agent.

In some aspects, the positioning step is accomplished by direct injection of the at least two populations of nanoparticles into the vicinity of the selected cells to be heated while in the alternative or in addition, the positioning step is accomplished by containing the at least two populations of nanoparticles within a microcatheter and positioning the contained at least two populations of nanoparticles in the vicinity of the selected cells to be heated, and/or the positioning step may be accomplished by injecting the at least two populations of nanoparticles within a body to be heated and subsequently concentrating the at least two populations of nanoparticles in the vicinity of the selected cells to be heated by application of a magnetic field.

DETAILED DESCRIPTION

Figure 1:
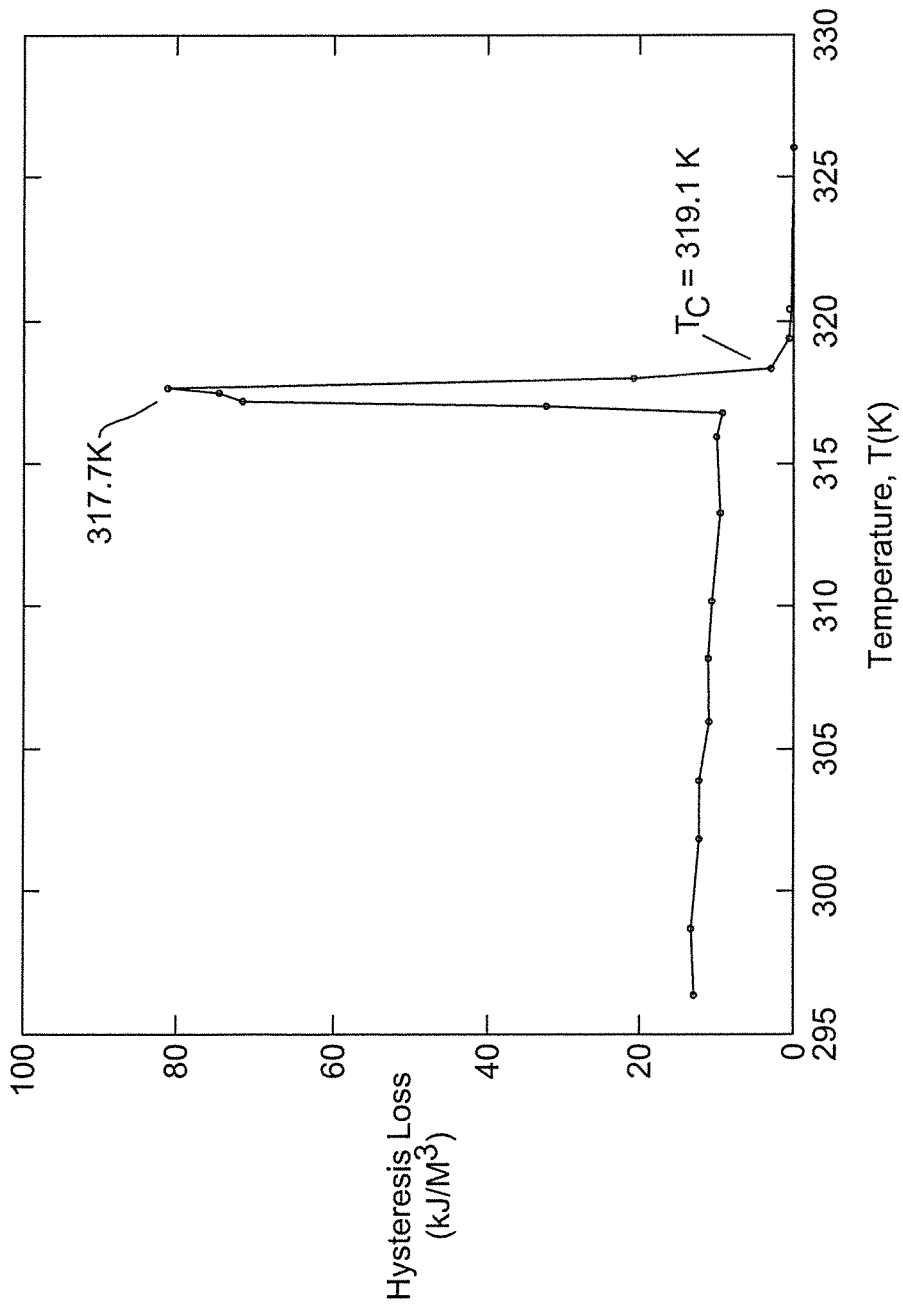
FIG. 1 illustrates the narrow range of temperatures for which an enhanced induction heating effect has been reported by Baratti et al. for $LaFe_{11.57}Si_{1.43}H_{1.75}$ ("Extraordinary induction heating effect near the first order Curie Transition", Applied Physics Letters 105 162412 (2014); 279 kHz and 8.8 kA/m.)

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

Although some suitable dimensions, ranges and/or values pertaining to various components, features and/or specifications are disclosed, one of skill in the art, incited by the present disclosure, would understand desired dimensions, ranges and/or values may deviate from those expressly disclosed unless the context clearly indicates an intended limitation.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an aspect", "some aspects", "other aspects", etc., indicate that the aspect described may include a particular feature, structure, or characteristic, but every aspect may not necessarily include the particular feature, structure, or characteristic. Moreover, such phrases are not necessarily referring to the same aspect. Further, when a particular feature, structure, or characteristic is described in connection with an aspect, it would be within the knowledge of one skilled in the art to effect such feature, structure, or characteristic in connection with other aspects, whether or not explicitly described, unless clearly stated to the contrary.

Within this specification and the appended claims, it will be understood that a reference to a Curie temperature of a population is understood to encompass variation within a population of nanoparticles such that the intent is to refer to the mean Curie temperature of the population if that qualifier is omitted.

FIG. 1 illustrates the change in static hysteresis loss as a function of temperature for a population of $LaFe_{11.57}Si_{1.43}H_x$ nanoparticles reported by Barati et al. ("Extraordinary induction heating effect near the first order Curie transition", Appl. Physics Letters 105, 162412 (2014)) at 279 kHz and 8.8 kA/m which illustrates both the narrow temperature range over which the enhanced induction heating effect has been observed and the abrupt cessation of hysteresis loss heating at the TC of the sample tested.

While the high SAR and appropriate TC of the $LaFe_{11.57}Si_{1.43}H_x$ materials make them attractive as agents for magnetic field induced hyperthermia treatment of selected cells, the narrow temperature range (~3° C.) associated with the observed SAR enhancement as well as the need to raise tissue temperatures to about 4 to 8° C. above adjacent, often core, body temperature, the requires a combination of longer exposure times, higher fields, and/or higher frequencies than would otherwise be desirable in treating a subject; however this difficulty may be overcome by employing two or more populations of injectable nanoparticles, which populations differ with regard to their TCs such that the narrow temperature ranges associated with the observed SAR enhancements below those TCs overlap and at least collectively span the temperature range between a core body temperature, nominally 37° C., and the desired hyperthermia temperature, typically either 41 to 45° C. or 41 to 47° C.

In contrast to more conventional hyperthermic treatment techniques using invasive probes that may result in local overheating inducing thermoablation and subsequent tissue necrosis, the hyperthermic implantable formulations developed by the present inventors are expected to deliver a rapid and self-limiting local heating with typical temperature increases in the range of 5° C. to 10° C. In some aspects, the available range of temperature increases may be even greater.

The use of a plurality of nanoparticle populations each having a different mean Curie point temperature and an enhanced SAR in the thermal region immediately below the mean Curie point temperature of the population is expected to result in rapid heating at relatively low magnetic field intensities such that the enhanced SAR exhibited by a first population of nanoparticles having a mean Curie temperature slightly above the ambient temperature of the selected cells to be heated will, upon excitation by an alternating magnetic field, heat the selected cells and the remaining populations of nanoparticles to the Curie temperature of the first population of nanoparticle, whereupon the induced heating of that first population of nanoparticles will cease as they reach their Curie temperature.

By selecting the mean Curie temperature of a second population of nanoparticles such that the enhanced SAR region immediately below the mean Curie temperature of the second population overlaps the mean Curie temperature of the first population of nanoparticles, it is possible to begin to excite the enhanced SAR region of the second population as the first population of nanoparticles becomes insensitive to further excitation by virtue of having reached its Curie temperature. The selection process may be extended to the inclusion of a third, fourth, fifth, sixth or more populations of nanoparticles as necessary to reach the desired treatment temperature. By employing a succession of populations of nanoparticles, each of which is within its enhanced SAR region as the temperature of the tissue to be heated is increased, it is expected that the overall time to reach an effective hyperthermia temperature may be decreased because heat generation will be enhanced at all temperatures up to the desired treatment temperature and yet the heating process will be self-limiting by the Curie temperature of the final population of nanoparticles to be activated as the temperature thus effectively preventing over heating.

Figure 2:
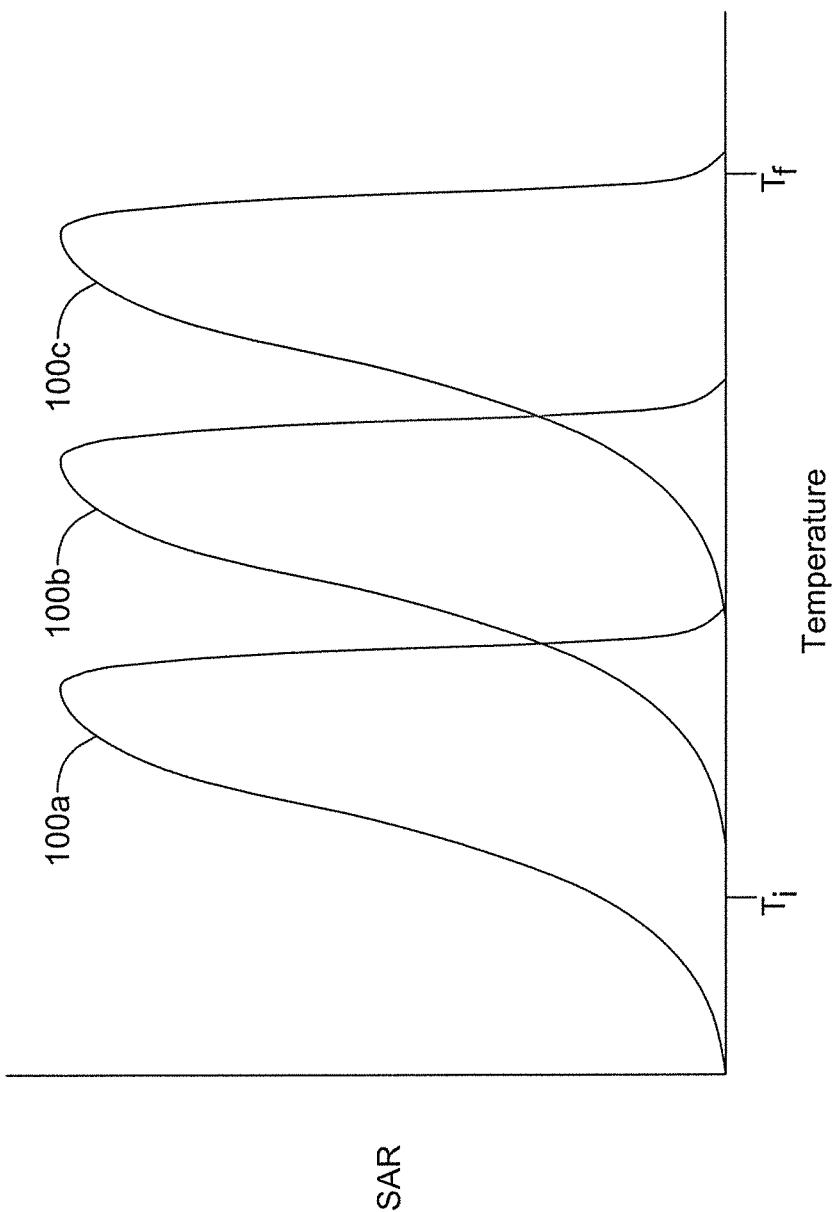
FIG. 2 somewhat schematically illustrates one aspect of the invention.

For example, if the region of enhanced SAR for a first population of nanoparticles has a temperature range of ~3° C., such as that of the $LaFe_{11.57}Si_{1.43}H_x$ materials described herein, and the selected cells to be heated have an initial temperature of 37° C., a first population of nanoparticles having a Curie temperature of 40° C. is expected to be efficiently heated by an appropriate alternating magnetic field to a temperature of 40° C. thereby raising the temperature of the selected cells and any remaining populations of nanoparticles to that temperature. When a second population of nanoparticles having a Curie temperature of 43° C. is also present with the selected cells at 40° C., the second population of nanoparticles is expected to be efficiently heated by an appropriate alternating magnetic field to a temperature of 43° C. thereby raising the temperature of the selected cells and any remaining populations of nanoparticles to that temperature. When a third population of nanoparticles having a Curie temperature of 45° C. is also present with the selected cells at 43° C., the third population of nanoparticles is expected to be efficiently heated by an appropriate alternating magnetic field to a temperature of 45° C. thereby raising the temperature of the selected cells and any remaining populations of nanoparticles to that temperature, thereby inducing apoptosis within the selected cells to be heated. This successive overlap of three populations of nanoparticles, each exhibiting the enhanced SAR effect immediately below the TC of the respective population, is illustrated somewhat schematically in FIG. 2 in which three populations of nanoparticles may be used to increase the temperature of a tissue environment from an initial temperature Ti to a final temperature Tf as the successive populations are heated by an applied alternating magnetic field having an appropriate frequency and magnetic field strength.

One of ordinary skill in the art would appreciate that the foregoing description is representative and not intended to be limiting. For example, it would be understood that the first population of nanoparticles may have a Curie temperature of 39.5° C.; a second population of nanoparticles may have a Curie temperature of 42° C.; a third population of nanoparticles may have a Curie temperature of 44.5° C.; and a fourth population of nanoparticles may have a Curie temperature of 47° C. if desired. Other combinations of populations of nanoparticles may be selected to span a desired temperature increase if the temperature range of the region of enhanced SAR is other than 3° C. In general, it is believed desirable to employ a minimal number of nanoparticle populations to span a given desired temperature increase in order to minimize the total mass of nanoparticles necessary to achieve the desired final temperature.

Figure 3:
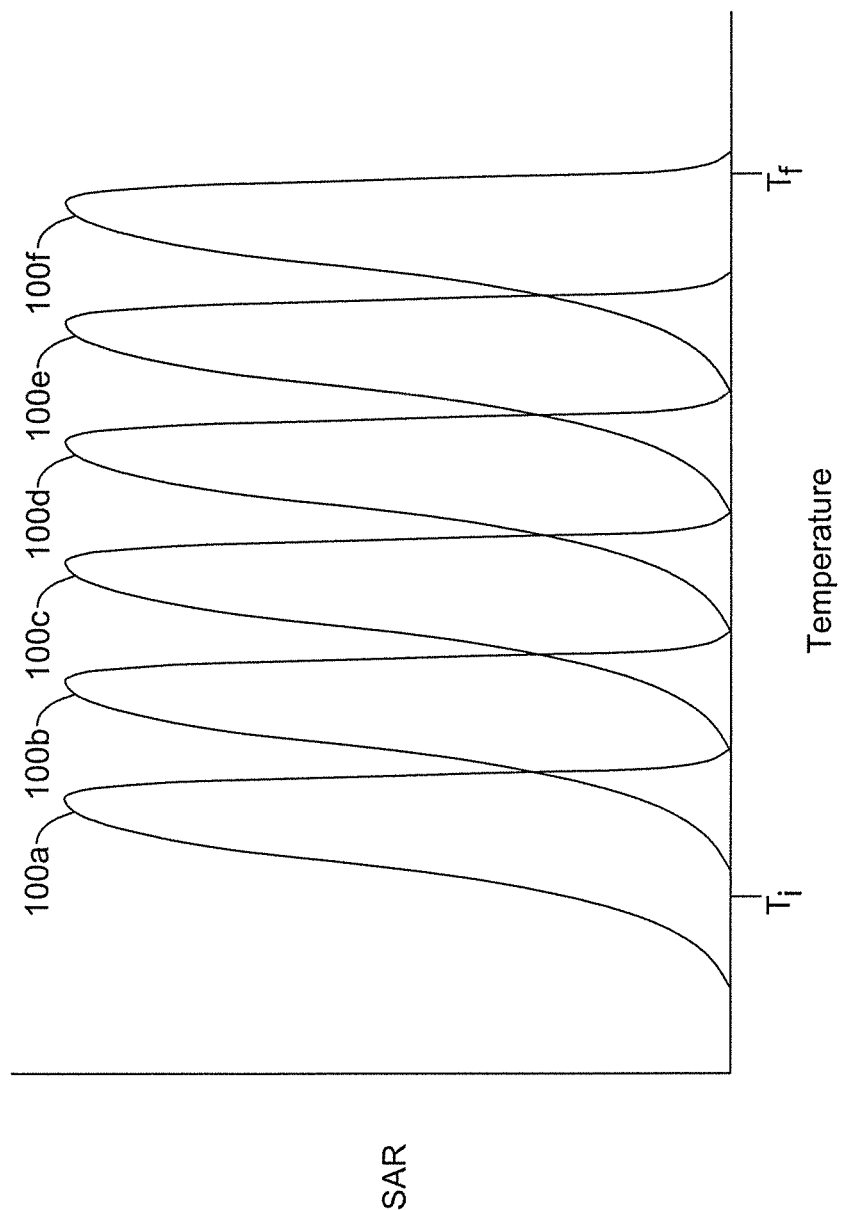
FIG. 3 somewhat schematically illustrates an alternate aspect of the invention.

If, for example, the initial temperature of tissue to be heated by this method, is different from 37° C. or a higher final temperature is desirable, a larger number of nanoparticle populations may be employed, such that a temperature increase of 12° C. is desirable, the result may be accomplished by employing six populations of nanoparticles, each of which is responsible for increasing the temperature of the tissue by approximately 2° C. This successive overlap of six populations of nanoparticles, each exhibiting the enhanced SAR effect immediately below the TC of the respective population, is illustrated somewhat schematically in FIG. 3 in which six populations of nanoparticles (100A to 100F) may be used to increase the temperature of a tissue environment from an initial temperature Ti to a final temperature Tf as the successive populations are heated by an applied alternating magnetic field having an appropriate frequency and magnetic field strength.

Figure 4:
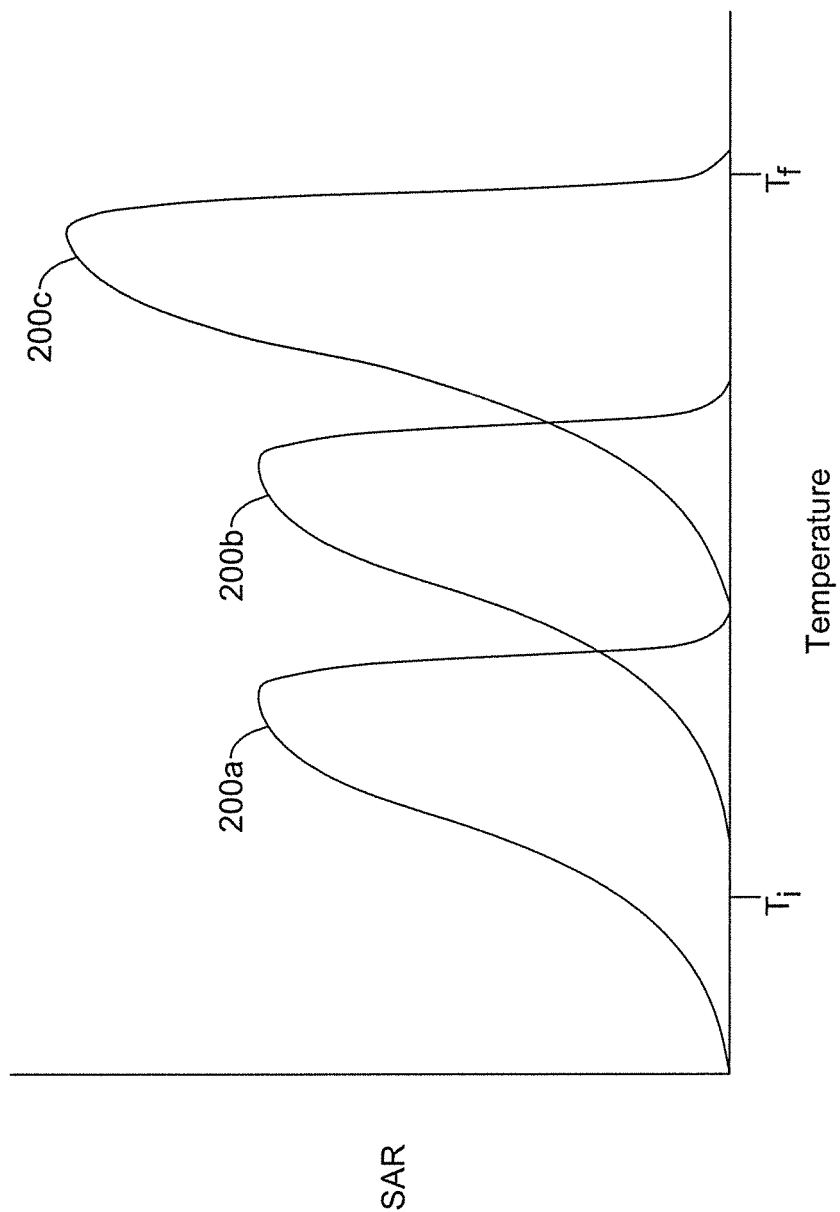
FIG. 4 somewhat schematically illustrates another aspect of the invention.

In addition to, or instead of, varying the number of populations employed, as in the examples given above, it is believed that different heating profiles may usefully be achieved by varying the ratios of the masses of the populations of nanoparticles. As an example, an initial temperature increase is accomplished by two smaller populations, 200A and 200B to attain a temperature above the initial or core tissue temperature, but below the temperature expected to result in significant apoptosis, followed by a larger population 200C which is expected to raise the tissue temperature more rapidly to a final temperature which will produce the desired apoptosis as illustrated somewhat schematically in FIG. 4. It will be appreciated that other combinations of unequal particle populations may be employed to achieve different heating profiles.

In some aspects, similar effects may be achieved by employing non-uniform spacing of the TCs of the populations of nanoparticles such that the number of nanoparticles which are subject to excitation with an enhanced SAR varies with temperature.

Figure 5:
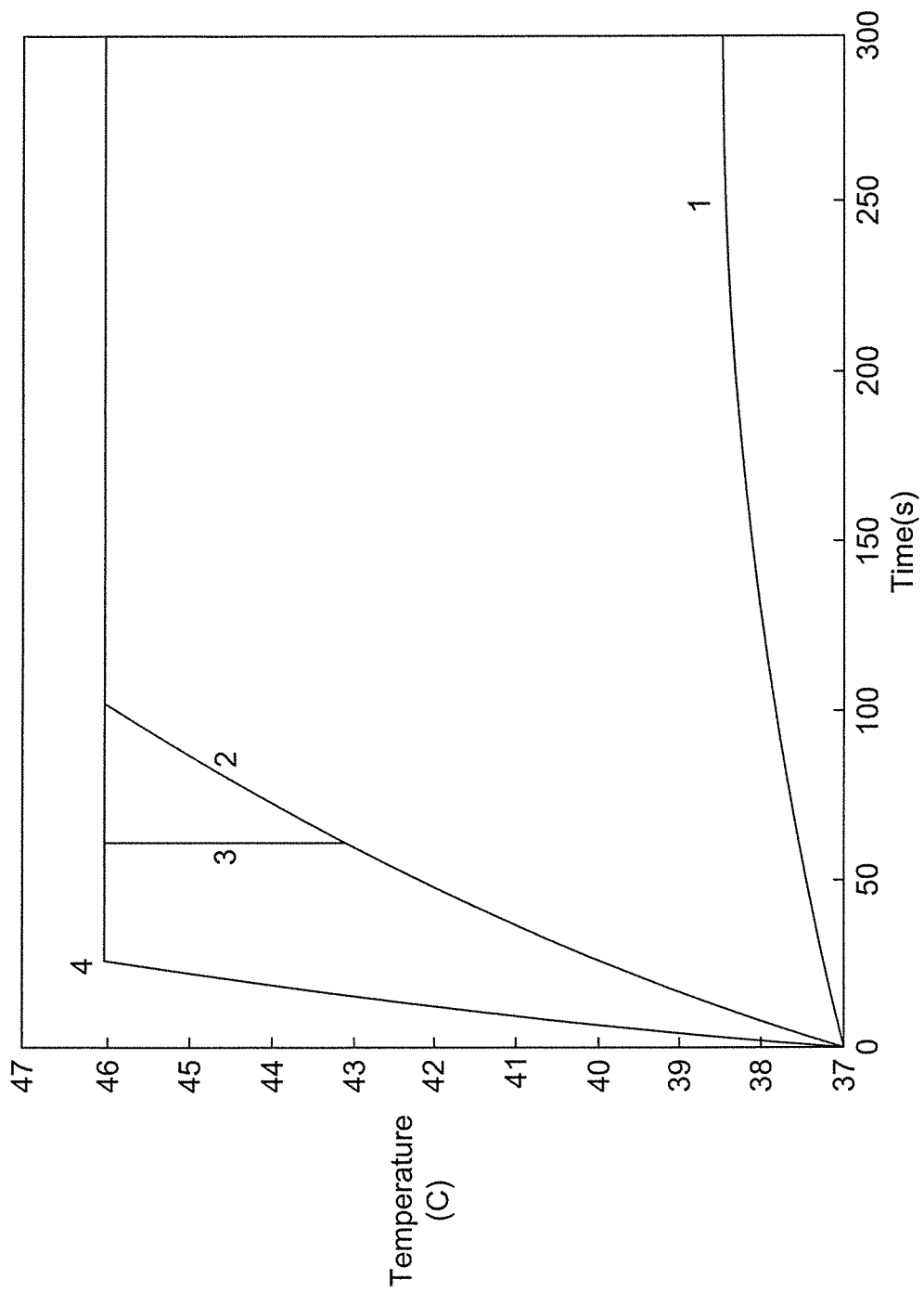
FIG. 5 illustrates simulated heating profiles for nanoparticle populations.

FIG. 5, illustrates comparisons of numerical simulations of expected temperature increases in which a single superparamagnetic nanoparticle population (1) is heated; in which enhanced SAR nanoparticle population heating has been modeled (2) using published data; in which the SAR of a population of $LaFe_{11.57}Si_{1.43}H_x$ nanoparticles having a 46° C. Curie temperature has been modeled (3); and in which the SAR of three combined populations of $LaFe_{11.57}Si_{1.43}H_x$ nanoparticles having TCs of 40, 43, and 46° C. have been modeled (4).

Figure 6:
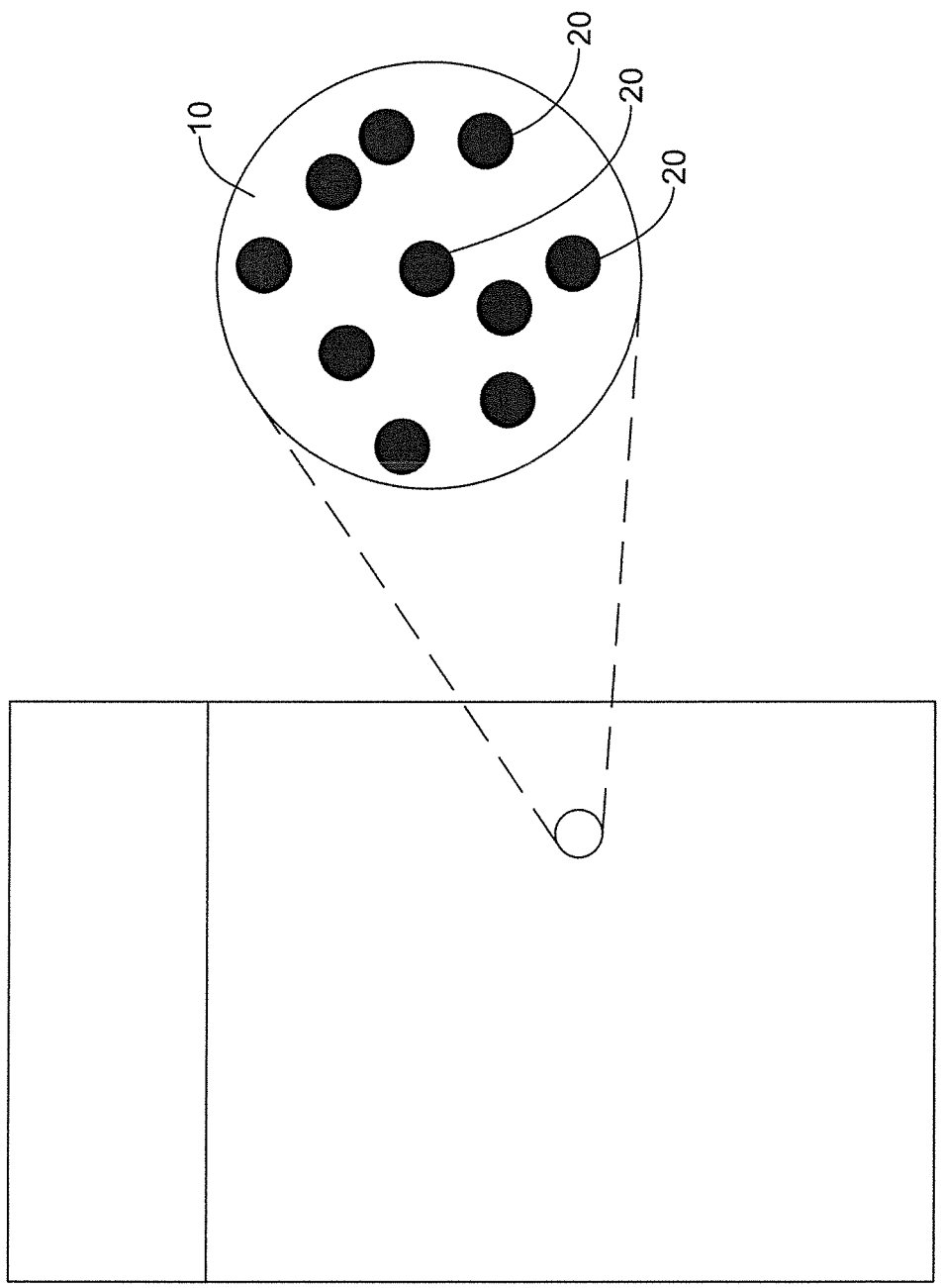
FIG. 6 illustrates an injectable dispersion of nanoparticles.

Positioning of the nanoparticle populations described may be accomplished by methods known in the art, for example, the nanoparticles 20 may be dispersed in a liquid carrier 10, as shown in FIG. 6 for delivery by direct injection, by injection of targetable particles into the general circulation, or by introduction within a microcatheter positioned adjacent to the tissue to be heated. In some aspects, the carrier 10 may be selected to precipitate, gel, polymerize, and/or be cross-linked once injected into the tissue.

Figure 7:
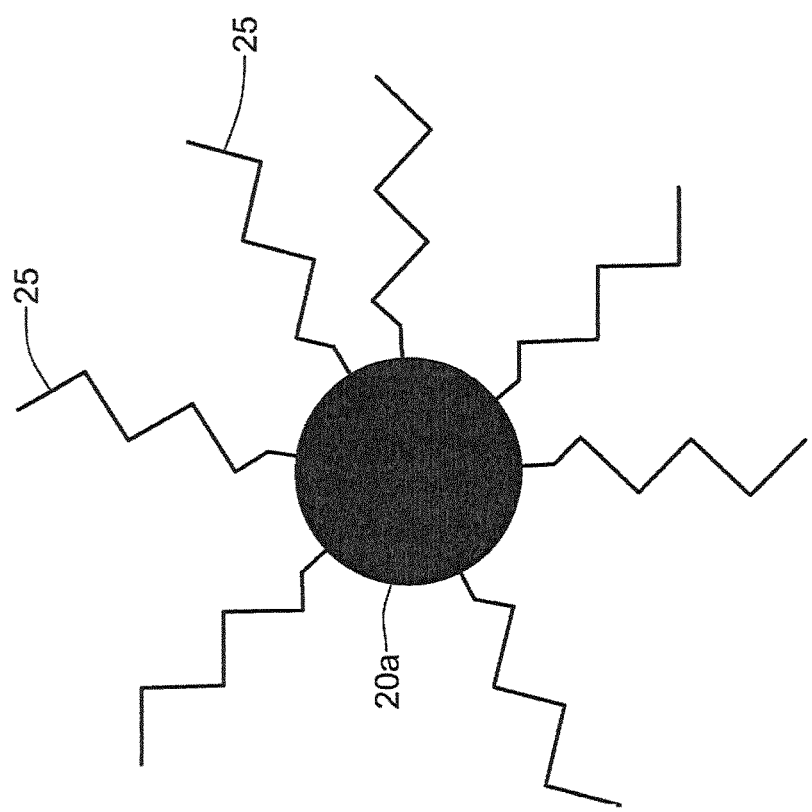
FIG. 7 illustrates schematically a nanoparticle of the invention which includes an attached therapeutic agent.

In some aspects, at least a portion of the particles 20A may include an attached therapeutic agent 25, as illustrated in FIG. 7, which in some aspects may be an anti-tumor agent. In such aspects, the carrier 10 may include compounds which enhance the activity of the anti-tumor agent.

Although the illustrative examples described above relate to $LaFe_{11.57}Si_{1.43}H_x$ nanoparticles useful for heating tissue, populations of other nanoparticles having an enhanced SAR region and/or other materials to be heated also are contemplated.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. An injectable formulation for magnetic field induced hyperthermia treatment of selected cells comprising:
   a liquid carrier; and
   at least a first population of nanoparticles and a second population of nanoparticles,
   wherein the first population of nanoparticles and the second population of nanoparticles each have a mean Curie temperature in the range of 37 to 47° C.; and
   wherein the mean Curie temperature of the first population of nanoparticles differs from the mean Curie temperature of the second population of nanoparticles by at least 2° C.;
   wherein the second population of nanoparticles comprises a region of enhanced specific absorption rate (SAR) below the mean Curie temperature of the second population of nanoparticles that overlaps the mean Curie temperature of the first population of nanoparticles; and
   wherein the region of enhanced SAR of the second population of nanoparticles that overlaps the mean Curie temperature of the first population of nanoparticles is configured to allow for excitation of the second population of nanoparticles within the enhanced SAR region of the second population of nanoparticles as the first population of nanoparticles becomes insensitive to further excitation by virtue of having reached its Curie temperature.

2. The injectable formulation of claim 1, wherein the first population of nanoparticles comprises a first region of enhanced specific absorption rate that is within 3° C. of the respective mean Curie temperature of the second population of nanoparticles; and
   wherein the second population of nanoparticles comprises a second region of enhanced specific absorption rate that is within 3° C. of the respective mean Curie temperature of the first population of nanoparticles.

3. The injectable formulation of claim 2, wherein an aggregate region including the first and second regions of enhanced specific absorption rate continuously span a temperature range of 5 to 10° C.

4. The injectable formulation of claim 3, wherein the aggregate region of enhanced specific absorption rate continuously spans a temperature range of 37 to 47° C.

5. The injectable formulation of claim 3, wherein the aggregate regions of the first or second enhanced specific absorption rate continuously spans a temperature range of 37 to 41° C.

6. The injectable formulation of claim 1, wherein the first and second populations of nanoparticles have compositions corresponding to $LaFe_{11.57}Si_{1.43}H_x$, wherein $0 < x \leq 2.27$.

7. The injectable formulation of claim 1, wherein the liquid carrier is selected from the group consisting of water, saline, dimethyl sulfoxide, ethanol, aqueous solutions of acetic acid, pyrrolidones, glycerol, and propylene glycol.

8. The injectable formulation of claim 7, wherein the liquid carrier further comprises an in situ polymerizing component.

9. The injectable formulation of claim 7, wherein the liquid carrier further comprises an in situ cross-linking component.

10. The injectable formulation of claim 7, wherein the liquid carrier further comprises a precipitating polymer component.

11. The injectable formulation of claim 1, wherein at least one of the first and second populations of nanoparticles include an attached therapeutic agent.

12. The injectable formulation of claim 11, wherein the therapeutic agent is an anti-tumor agent.

13. The injectable formulation of claim 1, further comprising a third, a fourth, a fifth, or a sixth populations of nanoparticles.

14. The injectable formulation of claim 13, wherein a mean Curie temperature of the third, fourth, fifth, or sixth population of nanoparticles differs from a mean Curie temperature of each of the remaining populations of nanoparticles by at least 2° C.

15. The injectable formulation of claim 13, wherein an enhanced SAR of any of the third, fourth, fifth, or sixth populations of nanoparticles overlaps at least one region of the enhanced SAR of any of the remaining populations of nanoparticles.

16. The injectable formulation of claim 1, further comprising a third population of nanoparticles having a mean Curie temperature in the range of 37 to 47° C.;
wherein the mean Curie temperature of the third population of nanoparticles differs from the mean Curie temperature of the second population of nanoparticles by at least 2° C.

17. The injectable formulation of claim 16, wherein the third population of nanoparticles comprises a region of enhanced specific absorption rate (SAR) below the mean Curie temperature of the third population of nanoparticles that overlaps the mean Curie temperature of the second population of nanoparticles.

18. A method of heating selected cells by magnetically induced hyperthermia comprising:
positioning two or more populations of nanoparticles in proximity to the selected cells to be heated, the two or more populations of nanoparticles comprising at least a first population of nanoparticles and a second population of nanoparticles in a liquid carrier;
subjecting the two or more populations of nanoparticles to an alternating magnetic field, thereby causing the two or more populations of nanoparticles to generate heat locally whereupon the selected cells experience hyperthermia;
wherein the first population of nanoparticles and the second population of nanoparticles each have a mean Curie temperature in the range of 37 to 47° C.;
wherein the mean Curie temperature of the first population of nanoparticles differs from the mean Curie temperature of the second population of nanoparticles by at least 2° C.;
wherein the second population of nanoparticles comprises a region of enhanced specific absorption rate (SAR) below the mean Curie temperature of the second population of nanoparticles that overlaps the mean Curie temperature of the first population of nanoparticles; and
wherein the region of enhanced SAR of the second population of nanoparticles that overlaps the mean Curie temperature of the first population of nanoparticles is configured to allow for excitation of the second population of nanoparticles within the enhanced SAR region of the second population of nanoparticles as the first population of nanoparticles becomes insensitive to further excitation by virtue of having reached its Curie temperature.

19. The method of claim 18, wherein the alternating magnetic field results in a specific absorption rate within the selected cells of no more than 2 W/kg.

20. The method of claim 8, wherein at least one of the two or more populations of nanoparticles releases a therapeutic agent.

21. The method of claim 18, wherein the positioning step is accomplished by direct injection of the at least two populations of nanoparticles into a vicinity of the selected cells to be heated.

22. The method of claim 18, wherein the positioning step is accomplished by containing the at least two populations of nanoparticles within a microcatheter and positioning the contained at least two populations of nanoparticles in a vicinity of the selected cells to be heated.

23. A method of heating selected cells by magnetically induced hyperthermia comprising:
positioning two or more small populations of nanoparticles in proximity to the selected cells to be heated, the two or more populations of nanoparticles comprising at least a first population of nanoparticles and a second population of nanoparticles in a liquid carrier;
subjecting the two or more populations of nanoparticles to an alternating magnetic field, thereby causing the two or more populations of nanoparticles to raise the temperature of the selected cells to a target hyperthermia temperature;
wherein the first population of nanoparticles and the second population of nanoparticles each have a mean Curie temperature in the range of 37 to 47° C.;
wherein the mean Curie temperature of the first population of nanoparticles differs from the mean Curie temperature of the second population of nanoparticles by at least 2° C.;
wherein the second population of nanoparticles comprises a region of enhanced specific absorption rate (SAR) below the mean Curie temperature of the second population of nanoparticles that overlaps the mean Curie temperature of the first population of nanoparticles; and
wherein the region of enhanced SAR of the second population of nanoparticles that overlaps the mean Curie temperature of the first population of nanoparticles is configured to allow for excitation of the second population of nanoparticles within the enhanced SAR region of the second population of nanoparticles as the first population of nanoparticles becomes insensitive to further excitation by virtue of having reached its Curie temperature.

* * * * *